(12) United States Patent
Amos et al.

(10) Patent No.: US 7,126,123 B1
(45) Date of Patent: Oct. 24, 2006

(54) SURFACE CONTAMINATION DETECTION METHOD AND APPARATUS

(75) Inventors: Jay M. Amos, Wichita, KS (US); Alan R. Gilbert, Newnan, GA (US)

(73) Assignee: Cessna Aircraft Company, Wichita, KS (US)

( * ) Notice: Subject to any disclaimer, the term of this patent is extended or adjusted under 35 U.S.C. 154(b) by 206 days.

(21) Appl. No.: 10/737,889

(22) Filed: Dec. 18, 2003

(51) Int. Cl.
*G01T 1/169* (2006.01)

(52) U.S. Cl. .................. 250/340; 250/301
(58) Field of Classification Search ............ 250/340, 250/301; 73/40.7
See application file for complete search history.

(56) References Cited

U.S. PATENT DOCUMENTS

| | | | |
|---|---|---|---|
| 4,863,268 A | | 9/1989 | Clarke et al. |
| 4,920,385 A | | 4/1990 | Clarke et al. |
| 5,087,822 A | | 2/1992 | Fairlie et al. |
| 5,347,128 A | * | 9/1994 | Puram et al. ............... 250/330 |
| 5,521,381 A | * | 5/1996 | Gregg et al. ............... 250/288 |
| 5,706,840 A | * | 1/1998 | Schneider et al. ........ 134/56 R |
| 5,822,054 A | | 10/1998 | Coulthard |
| 6,605,807 B1 | * | 8/2003 | Safai ...................... 250/341.1 |
| 6,856,403 B1 | * | 2/2005 | Welch et al. ............... 356/492 |
| 6,956,228 B1 | * | 10/2005 | Shelley et al. ........... 250/559.4 |
| 2005/0076706 A1 | * | 4/2005 | Sergoyan ..................... 73/40.7 |

OTHER PUBLICATIONS

Ellis, Brian, "The Water Break Test," 2005, Emerald Group Publishing Limited, pp. 47-50.*

* cited by examiner

*Primary Examiner*—Otilia Gabor
*Assistant Examiner*—Christine Sung
(74) *Attorney, Agent, or Firm*—Robert O. Blinn

(57) ABSTRACT

A method and an apparatus for inspecting parts for surface contamination including the steps of covering the part with a film of water, and then scanning the wetted part with a infrared camera to preserve the reflected image of the reflected infrared light thereby defining a water break area of contamination.

8 Claims, 2 Drawing Sheets

SURFACE CONTAMINATION DETECTION METHOD AND APPARATUS

FIELD OF THE INVENTION

The present invention relates to method and apparatus for inspecting for surface contamination on dense material part surfaces prior to secondary operations such as bonding, painting, anodizing or plating.

BACKGROUND OF THE INVENTION

There are a variety of applications for inspecting the surface cleanliness of manufactured products. A variety of systems have been developed to inspect a multiplicity of surfaces for irregular surfaces as well as contaminants on the surface such as painted panels in the automotive and appliance fields. Some of these surface inspection processes are looking for flaws in the surface or surface finish and also contamination on the surface such as oils or other organic residue. U.S. Pat. No. 4,920,385 is a flaw inspection system that used on sheet materials including aircraft panels for determining surface defects in the panel by reflecting an image of visible light off the irregular surface and thus creating a wavy image in an oppositely positioned camera of the defect. There are numerous other optical methods of measuring the smoothness or contour of a part by imaging a grill or grid of lines on the reflected image of the panel, which become irregular once reflected off an irregular surface.

U.S. Pat. No. 4,863,268 teaches a similar surface detection system to the previous patent for automobile parts for detecting irregularities in the surface of the panel. The source of light and camera are both oriented in the same direction while the reflective surface on the part is used to direct light from the surface being inspected back to the camera. The area of inspection is, of course, very small with only a single light source and a single camera. Such a system would not be particularly useful in inspecting large areas of aluminum aircraft panels of the present invention.

U.S. Pat. No. 5,087,822 teaches another reflection type of inspection system which detects irregularies in the surface of a metal sheet with the use of multiple lamps which reflect visible light sources from different positions off of a sheet being inspected to a single camera. U.S. Pat. No. 5,822,054 detects the presence of defects in the surface of a metal sheet by the same reflective image concept discussed above except by a human inspector. None of the above patents utilize variations in infrared emissivity as a means to detect contamination on the surface nor do any utilize the water break test.

SUMMARY OF THE INVENTION

The present invention is a contamination detection method utilizing infrared (IR) light with the old and well-established water break test. The contaminants concerned with the present method include oil, grease and other organic compounds, as well as inorganic materials, which are typically used in the manufacturing and forming of aircraft parts and skins.

The water break test involves spraying or dipping a part or panel in a water rinse following a cleaning operation wherein the water forms a continuous film over the clean portion of the panel, however, due to the reduced surface tension between the water and oil or grease, the water film will break around the contaminated areas and leave no water film. This water break test has been used for years in wet chemical processes in aerospace and other industries; however, it requires a visual inspection of the panels and parts during the deoxidizing and alkaline cleaning steps, which is quite hazardous to humans due to the use of various caustic and acid chemical processes. Visual inspection of the water break test is sometimes difficult unless lighting and viewing orientation is carefully controlled while the IR image has substantial contrast, therefore, an automated IR camera inspection system is highly desirable over the current manual visual inspection for various reasons.

Infrared cameras are used to inspect the wetted surface of large parts or skins. The camera resolution and infrared emissivity properties permits the inspection of large contoured metal skins rapidly and without contact for online process monitoring. Digital images are amenable to automated defect recognition in image analysis for a highly reliable and automated inspection system with infrared cameras.

In the choice of infrared (IR) cameras, they include a near IR range between 0.9 and 1.7 µm wavelength, a mid range of 1.7-to 7 µm, and a long range between 7 and 14 µm. One skilled in the art would normally think that a near range IR infrared range camera would be most suitable for detecting organic contaminants since there is an absorption notch around 0.3 µm which provides the optimum separation between bare metal and a fluid covered surface, however, due to the low emmisivity of bare metal surfaces, a long IR range of 7–14 µm has been found to be more appropriate being less sensitive to background lighting and surface reflections. In the prior art, they have utilized infrared spectroscopy for inspecting very small samples such as wafers and chips, which involve a very costly and intrusive instrumentation techniques. The long IR range cameras can be used continuously for long periods of time without shortened life since they don't require cooling which near IR cameras require. Other work has involved laser-based FTIR spectroscopy, but are also limited to only organic contaminates, small areas and slow speed. Due to the diffuse properties of water, the angle of incidence is not particularly sensitive in infrared wavelengths (±80 degrees), therefore; the positioning of the camera is not critical. Furthermore, parts with complex shapes can be inspected easily from a single point of view.

The process lines for cleaning and inspection of aircraft parts involve a hoist and a bridge crane which lifts and lowers a series of vertically positioned frames in and out of chemical and rinsing tanks, which in turn support the parts therebetween by suspending wires or other means later discussed. These frames can be over 30 feet in width and 6 feet in height and can be inspected by a single or multiple IR cameras, which can be stationary or moving. A moving camera can be programmed to move quickly over the total area of the supporting frame, which can be mounted in various locations. The infrared image of the water break condition provides is a very clearly defined area with the clean area appearing black due to high emissivity and the contaminated areas appearing light gray or white (low emissivity). A rough surface of a part inspected which is clean of contaminants provides no problem to the infrared inspection since the surface tension between the water and metal is approximately the same.

Removal of surface contamination on aircraft parts and skins is critical for not only bonding the parts together, but also preventing corrosion. An inadequate bond of the primary adhesive caused by surface contamination can cause structural failure in the bonded joint. Also, organic contamination can prevent deoxidizing the surface of the part completely as well as the anodizing process thus weakening the bonded joint.

While the inspection process is used specifically on metal parts, it could also be used on ceramic or polymer parts as well that have comparable surface tensions. The principal object of the present invention to provide an automated surface contamination detecting method to more effectively detect surface contamination without visual inspection.

Another object of the present invention is to provide an infrared inspection method for water break on aluminum panels, which are clearly defined.

An automated inspection system is highly desirable over the current manual visual inspection with the water break test due to the hazardous conditions present around chemical processing where inspections must be performed. Focal plane array infrared cameras are used to inspect the wetted surface of large parts or skins due to the camera's resolution and infrared emissivity properties, it is quite practical to inspect a large metal skin rapidly. The contaminated areas that are thinly wetted or dry are greatly enhanced compared to the visible light inspection due to the large change in emissivity between water film and the dry metal surface. Digital images are amenable to automated defect recognition and image analysis for a highly reliable and automated inspection system with these infrared cameras.

DETAILED DESCRIPTION OF THE PREFERRED EMBODIMENT

Figure 1:
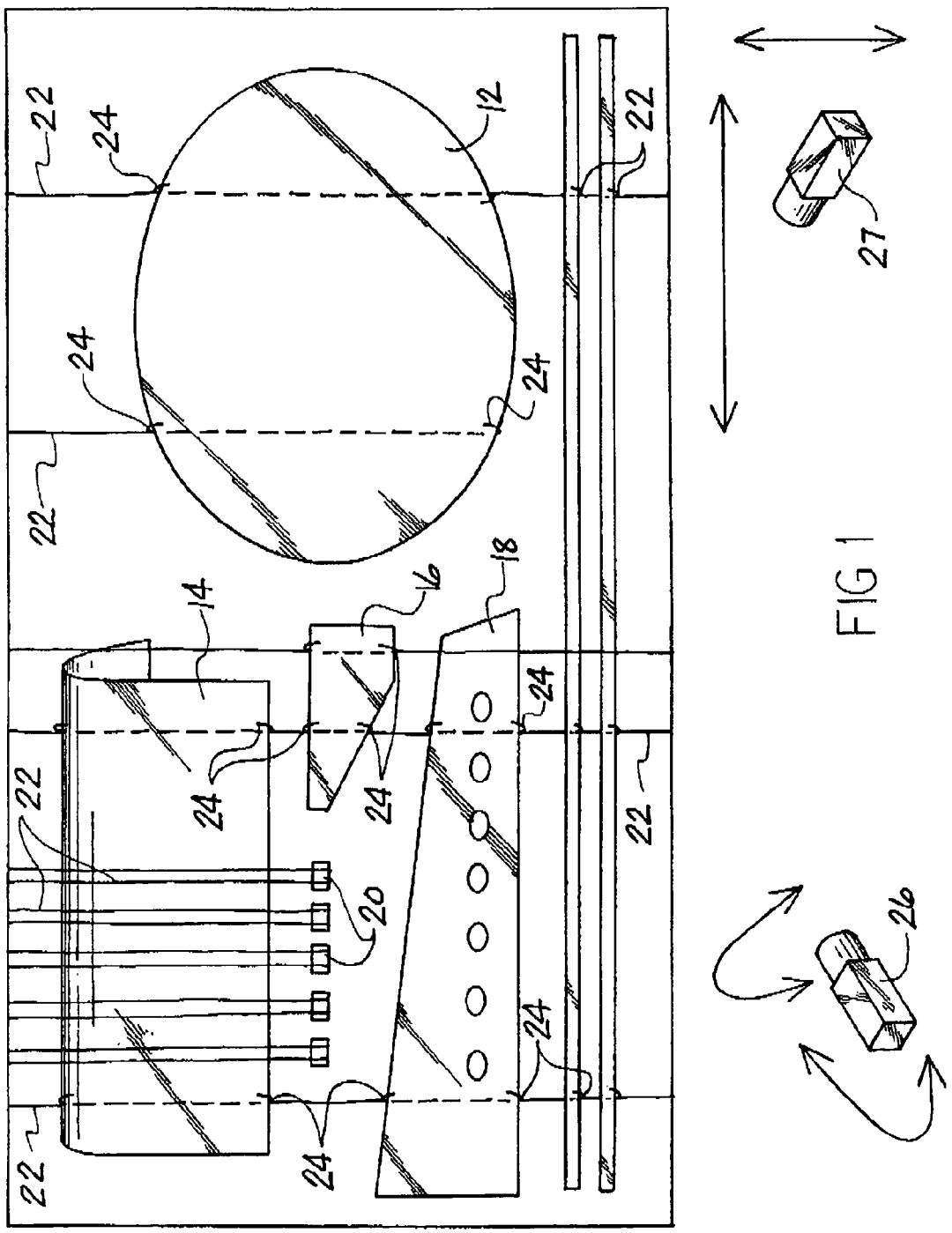
FIG. 1 is a symbolic front elevational view of a rack supporting a plurality of parts for inspection; and, FIG. 2 is a symbolic perspective view from above of a basket containing parts to be inspected.

FIG. 1 is a symbolic representation of the supporting frame 10 which is supporting a variety of aircraft skins and parts 12, 14, 16, 18, and 20. The various parts are suspended within frame 10 by a series of wires 22 which are typically twisted around the part to support same, such as portions 24 which engage the part. Various curved shaped parts, such as part 14, can be examined by the present inspection process by infrared cameras 26 and 27 which have sufficiently focal distance to examine a relatively large area without movement. Cameras 26 and 27 can be fixed mounted on a pan/tilt head so as to scan the entire length of frame 10 which can be dimensioned over 30 feet in length. One of the cameras 26 or 27 can be positioned on the opposite side of support frame 10 so as to examine both sides of the part simultaneously. Frame 10 can be made of tubular steel as well as other materials, which could be impervious to various alkaline and acid dip tanks. The frames 10 are lifted and lowered by its upper horizontal frame member 11 through a conventional hoist and bridge crane which are not shown in the drawings, but are well known in the art. The frames are passed through a series of alkaline, water rinse, deoxidizing and acid dip tanks.

Figure 2:
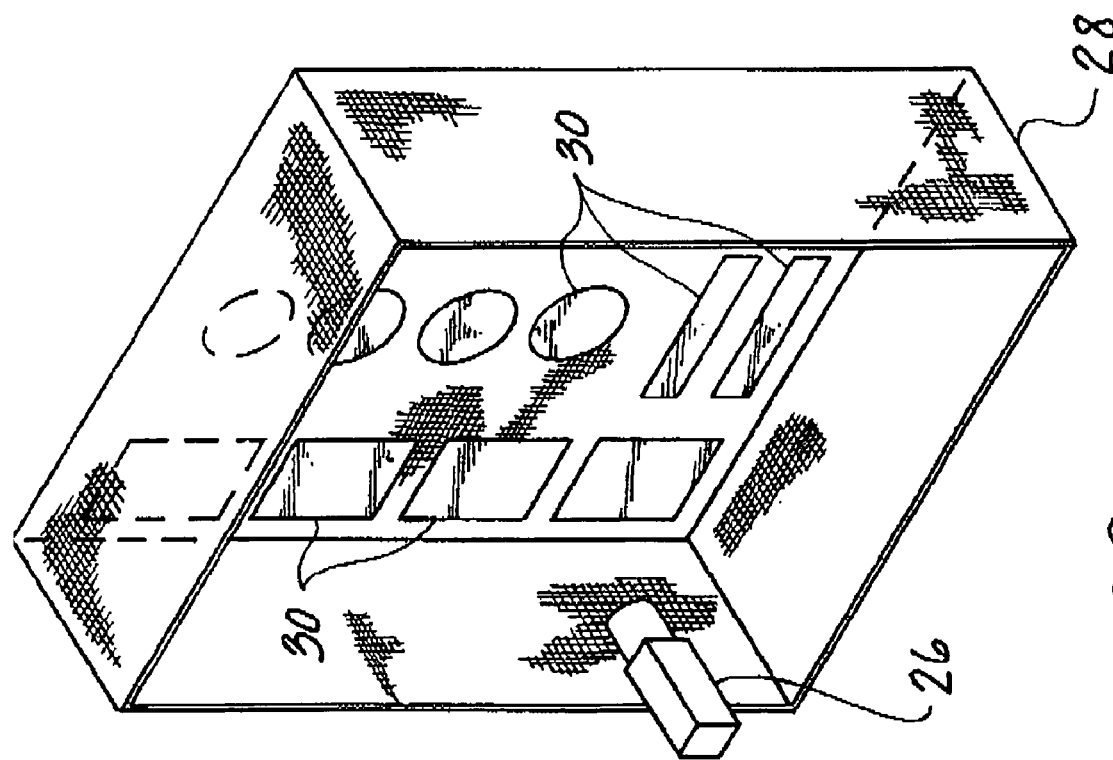

FIG. 2 illustrates a alternate source of support for metal parts being inspected with the use of a wire mesh basket 28 which includes a series of parts 30 which merely rest on the horizontal bottom surface of the basket. A contaminate free part will give solid black infrared image as shown by parts 30 in FIG. 2.

Figure 3:
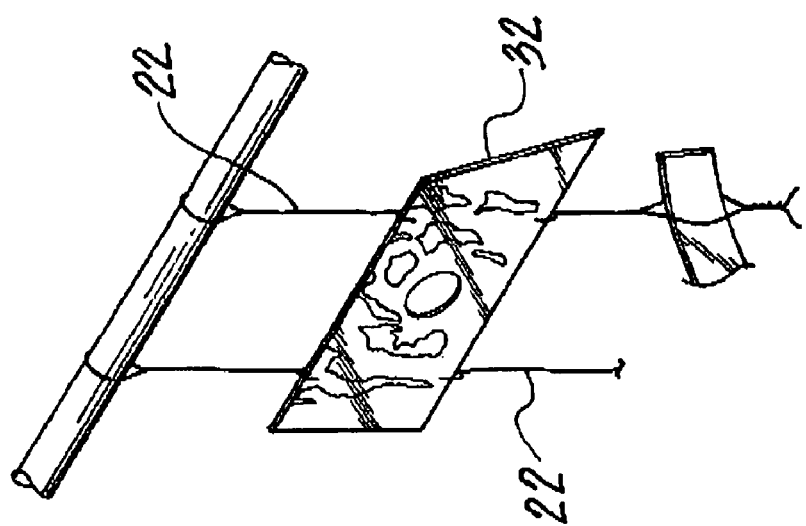
FIG. 3 is an actual infrared image of a contaminated part.

FIG. 3 is an actual infrared image of a contaminated part 32 supported by a series of wires 22. The contamination areas are shown as a series of white areas on the part which can readily be identified and again passed through the cleaning process before being inspected again.

Operation

In the cleaning process for newly manufactured aircraft skins and parts, the parts are mounted on a supporting frame or rack 10 which are first inserted in a degreasing and alkaline bath and then a rinse bath before the parts are dipped in a deoxidizing bath of low strength acid which are then rinsed before being inspected by infrared cameras 26 or 27.

It is noted that this invention is useful not only on aircraft parts but also various other formed or cast sheet metal parts utilized in all other fields such as for example, automotive or consumer appliances.

We claim:

1. A method of inspecting the surface of a part for surface contamination comprising the steps of:
   dipping the part in a water rinse tank;
   exposing the part to a 7–14 µm wave length infrared camera to preserve an image of infrared emitted energy; and
   defining a water break area of contamination using said image.

2. A method of inspecting the surface of a metal part, as set forth in claim 1, including the step of mounting the part to be inspected on a frame with wires supporting the part between the periphery of the frame.

3. A method of inspecting the surface of a part, as set forth in claim 1, including the step of placing the part to be inspected in a wire basket.

4. An apparatus for inspecting a part for surface contamination comprising:
   a water rinse tank for dipping said part; and,
   an infrared camera for scanning a source of infrared energy distribution from the part and defining a water break area of contamination on the part.

5. An apparatus for inspecting, as set forth in claim 4, wherein the infrared camera is a long 7–14 µm wavelength camera.

6. An apparatus, as set forth in claim 4, wherein the metal part is sprayed rather than dipped in a water rise tank.

7. A method of inspecting the surface of a metal part for surface contamination comprising the steps of:
   covering the metal part with a film of water;
   scanning the part with an infrared camera;
   using said camera to receive an image generated from emitted infrared energy; and
   defining a water break area of contamination on said part using said image.

8. A method of inspecting the surface of a metal part, as set forth in claim 7, wherein the camera is a long 7–14 µm wavelength camera.

* * * * *